United States Patent [19]

Barile et al.

[11] Patent Number: 4,584,422

[45] Date of Patent: Apr. 22, 1986

[54] SELECTIVE ALKYLATION OF XYLENES WITH ETHYLENE

[75] Inventors: George C. Barile, South Somerville; Warren W. Kaeding, Westfield, both of N.J.

[73] Assignee: Mobil Oil Corporation, New York, N.Y.

[21] Appl. No.: 391,279

[22] Filed: Jun. 23, 1982

Related U.S. Application Data

[63] Continuation of Ser. No. 46,394, Jun. 6, 1979, abandoned.

[51] Int. Cl.[4] ................................................ C07C 3/52
[52] U.S. Cl. ..................................... 585/467; 585/481
[58] Field of Search ................................ 585/467, 481

[56] References Cited

U.S. PATENT DOCUMENTS 3,855,331 12/1974 Moss, Jr. et al. ............... 260/669 R
4,094,921 6/1978 Kaeding et al. ..................... 585/467
4,100,214 7/1978 Dwyer ............................... 585/481
4,128,592 12/1978 Kaeding ............................. 585/467

OTHER PUBLICATIONS

"Selective Disproportionation of Alkylbenzenes Over Mordenite Molecular Sieve Catalyst", *Journal of Catalysis* 19, 394–397 (1970), Sigmund M. Csicsery.

*Primary Examiner*—Curtis R. Davis
*Attorney, Agent, or Firm*—Alexander J. McKillop; Michael G. Gilman; Edward F. Kenehan, Jr.

[57] ABSTRACT

A process for the production of 3,4-dimethyl-1-ethylbenzene by selective alkylation of dimethylbenzene with ethylene. The process is carried out in the presence of a crystalline zeolite catalyst having a silica to alumina mole ratio of at least about 12 and a Constraint Index of greater than 2 and up to about 12.

23 Claims, No Drawings

SELECTIVE ALKYLATION OF XYLENES WITH ETHYLENE

This is a continuation of application Ser. No. 046,394 filed June 6, 1979, now abandoned.

BACKGROUND OF THE INVENTION

1. Field of the Invention

This invention is concerned with a method for the selective preparation of 3,4-dimethyl-1-ethylbenzene from xylene and ethylene utilizing a shape selective zeolite catalyst.

2. Description of the Prior Art

Six structural isomers of the compound dimethylethylbenzene are known to exist. The names, structures, boiling points and equilibrium distribution at 315° C. of these isomers are as shown below in Table I.

TABLE I

| Name and Structure | Boiling Point, °C. | Equilibrium % at 315° C.* |
|---|---|---|
| 2,3-Dimethyl-1-ethylbenzene 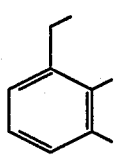 | 193.9 | 3.2 |
| 2,4-Dimethyl-1-ethylbenzene 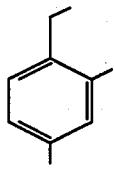 | 188.4 | 16.4 |
| 2,5-Dimethyl-1-ethylbenzene 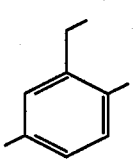 | 186.9 | 23.9 |
| 2,6-Dimethyl-1-ethylbenzene 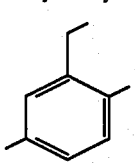 | 190.0 | 1.9 |
| 3,4-Dimethyl-1-ethylbenzene 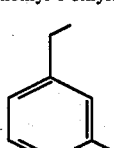 | 189.8 | 20.9 |
| 3,5-Dimethyl-1-ethylbenzene  | 183.8 | 33.7 |
| 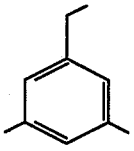 | | |

*S. Csicsery, J. of Catalysis, 19, 394 (1970)

A process for the synthetic manufacture of these compounds via ethylation of xylene or of mixed xylenes in the presence of aluminum chloride is disclosed in U.S. Pat. No. 3,855,331 to Moss et al. However, the data disclosed therein demonstrates that even at low temperatures alkylation is not selective for any particular isomer of dimethylethylbenzene. Other literature on the transalkylation of 2-ethyltoluene on H-Mordenite [S. Osicsery, Journal of Catalysis, 23, 124 (1971)] indicates that this zeolite is not particularly shape selective for the production of 3,4-dimethyl-1-ethylbenzene, yielding only 30% to 50% at between 200° C. and 300° C.

3,4-Dimethyl-1-ethylbenzene is an intermediate useful for the production of 3,4-dimethylstyrene. A process for the selective production of 3,4-dimethyl-1-ethylbenzene would eliminate the expense and waste of presently employed processes for isolating this isomer from equilibrium mixtures of the various dimethylethylbenzenes.

SUMMARY OF THE INVENTION

We have now discovered a process for the selective production of primarily a single desirable isomer of the six possible dimethyethylbenzenes (i.e. 3,4-dimethyl-1-ethylbenzene). The process generally involves the alkylation of xylene and rearrangement of the various dimethylethylbenzene isomers utilizing a particular type of crystalline zeolite catalyst thereby eliminating complex separation problems. Zeolite catalysts useful herein are characterized as having a silica to alumina ratio of at least about 12 and a Constraint Index, as hereinafter defined, of greater than 2 and up to about 12. The catalysts employed demonstrate a remarkable shape selectivity to the 3,4-isomer among the various dimethylethylbenzene isomers, with the level of catalyst activity and selectivity being somewhat dependent on crystal size and steam modification.

The process may be carried out by contacting the reactants with the catalyst at a temperature of about 250° C. to about 600° C. and a pressure of about $10^4$ $N/m^2$ to $10^7$ $N/m^2$ (0.1–100 atmospheres). The preferred temperatures and pressures will fall within the approximate ranges of 300° C. to 450° C. and $10^5$ to $4 \times 10^6$ $N/m^2$, respectively. The preferred catalyst for utilization herein comprises HZSM-5 crystalline zeolite.

DESCRIPTION OF SPECIFIC EMBODIMENTS

The crystalline zeolites utilized herein are members of a novel class of zeolitic materials which exhibit unusual properties. Although these zeolites have unusually low alumina contents, i.e. high silica to alumina mole ratios, they are very active even when the silica to alumina mole ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning with oxygen-containing gas such as air.

An important characteristic of the crystal structure of this class of zeolites is that it provides constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon or aluminum atoms at the centers of the tetrahedra. Briefly, the preferred type zeolites useful in this invention possess, in combination: a silica to alumina mole ratio of at least about 12 and a structure providing constrained access to the intracrystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. In addition, zeolites as characterized herein which are substantially free of aluminum, i.e. having silica to alumina mole ratios of 1,600 and higher, are found to be useful and even preferable in some instances. Such "high silica" zeolites are intended to be included within this description.

The zeolites useful in this invention have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although it is thought that 12-membered rings usually do not offer sufficient constraint to produce advantageous conversions, it is noted that the puckered 12-ring structure of TMA offretite does show constrained access. Other 12-ring structures may exist which may be operative and, therefore, it is not the present intention to judge the usefulness herein of a particular zeolite solely from theoretical structural considerations.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a small sample, approximately one gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon pear volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of greater than 2 and up to about 12. Constraint Index (CI) values for some typical zeolites are:

| ZEOLITE | C.I. |
|---|---|
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| TMA Offretite | 3.7 |
| Beta | 0.6 |
| H—Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Therefore, it will be appreciated that it may be possible to so select test conditions as to establish more than one value in the preferred range of >2 and up to 12 for the Constraint Index of a particular zeolite. Such a zeolite exhibits the constrained access as herein defined and is to be regarded as having a Constraint Index of >2 and up to 12. Also contemplated herein as having a Constraint Index of 1 to 12 and therefore within the scope of the novel class of highly siliceous zeolites are those zeolites which, when tested under two or more sets of conditions within the abovespecified ranges of temperature and conversion, produce a value of the Constraint Index slightly less than the preferred lower limit, e.g. 1.9, or somewhat greater than 12, e.g. 14 or 15, with at least one other value within the range of greater than 2 and up to 12. Thus, it should be understood that the Constraint Index value as used herein is an inclusive rather than an exclusive value. That is, a zeolite, when determined by any combination of conditions within the testing definition set forth hereinabove to have a Constraint Index of in excess of 2 and up to 12, is intended to be included in the instant catalyst definition regardless that the same identical zeolite, when tested under other of the defined conditions, may give a Constraint Index value outside of >2 and up to 12.

The class of zeolites defined herein is exemplified by ZSM-5, ZSM-11, ZSM-23, ZSM-35, and other similar materials. Zeolite catalyst ZSM-5 is described in detail in U.S. Pat. Nos. 3,702,886 and 3,941,871. The entire descriptions contained within those patents, particularly the X-ray diffraction pattern of therein disclosed ZSM-5, are incorporated herein by reference.

The zeolite ZSM-11 is described in U.S. Pat. No. 3,709,979. That description, and in particular the X-ray diffraction pattern of said ZSM-11, is incorporated herein by reference.

ZSM-23 is described in U.S. Pat. No. 4,076,842. The entire content thereof, particularly the specification of the X-ray diffraction pattern of the disclosed catalyst, is incorporated herein by reference.

ZSM-35 is described in U.S. Pat. No. 4,016,245. The description of that catalyst, and particularly the X-ray diffraction pattern thereof, is incorporated herein by reference.

It is to be understood that by incorporating the reference the foregoing patents to describe the preferred catalysts with greater particularity, it is intended that identification of the therein disclosed crystalline zeolites be resolved solely on the basis of their X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the silica-alumina mole ratios discussed therein. It is the crystal structure, as identified by the X-ray diffraction "fingerprint", which establishes the identity of the crystalline zeolite catalyst.

The specific zeolites described, when prepared in the presence of organic cations, are substantially catalytically inactive, possibly because the intracrystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to this type zeolite catalyst by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-23, and ZSM-35, with ZSM-5 being particularly preferred.

In a preferred aspect of this invention, the zeolites hereof are selected as those having a crystal framework density, in the dry hydrogen form, of not less than about 1.6 grams per cubic centimeter. It has been found that zeolites which satisfy all three of these criteria are most desired for several reasons. When hydrocarbon products or by-products are catalytically formed, for example, such zeolites tend to maximize the production of gasoline boiling range hydrocarbon products. Therefore, the preferred zeolites of this invention are those having a Constraint Index as defined above of in excess of 2 and up to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article on *Zeolite Structure* by W. M. Meier. This paper, the entire contents of which are incorporated herein by reference, is included in "Proceedings of the Conference on Molecular Sieves, London, April 1967," published by the Society of Chemical Industry, London, 1968.

When the crystal structure is unknown, the crystal framework density may be determined by classical pyknometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |

-continued

| Zeolite | Void Volume | Framework Density |
|---|---|---|
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

In practicing the desired conversion process, it may be desirable to incorporate the above-described crystalline zeolite with another material resistant to the temperature and other conditions employed in the process. Such matrix material is useful as a binder and imparts greater resistance to the catalyst for the severe temperature, pressure and reactant feed stream velocity conditions encountered in many cracking processes.

Useful matrix materials include both synthetic and naturally occurring substances, as well as inorganic materials such as clay, silica and/or metal oxides. The latter may be either naturally occurring or in the form of gelatinous precipitates or gels, including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix on an anhydrous basis may vary widely, with the zeolite content ranging from between about 1 to about 99 percent by weight and more usually in the range of about 5 to about 80 percent by weight of the dry composite.

The preferred crystalline zeolite catalysts useful herein may desirably be modified by steaming. Such treatment entails contacting the zeolite with an atmosphere containing from about 5% to about 100% steam at a temperature of from about 250° C. to about 1000° C. for a period of between about 0.25 and about 100 hours and under pressures ranging from subatmospheric to several hundred atmospheres.

Another modifying treatment involves precoking of the catalyst to deposit a coating of between about 2% and about 75%, and preferably between about 15% and about 75% by weight of coke thereon. Precoking can be accomplished by contacting the catalyst with a hydrocarbon charge, e.g. toluene, under high severity conditions or, alternatively, at a reduced hydrogen to hydrocarbon concentration (i.e. 0 to 1 mole ratio of hydrogen to hydrocarbon) for a sufficient time to deposit the desired amount of coke thereon.

It has been found that the level of activity and the degree of selectivity of the preferred catalyst is dependent to some degree on the crystal size of the catalyst. Catalysts useful in the present process include a range of crystal sizes from about 0.01 to about 40 microns. The smaller crystal sizes are the most preferred in that they have been found to give the most desirable level of selectivity to the 3,4-isomer. Although crystal sizes within the entire range as set out above have been found to be useful, the most preferred catalysts will be those having a crystal size within the range of about 0.01 to 2 microns.

Alkylation of xylene in the presence of the above-described catalyst is effected by contact of the xylene with ethylene at a temperature of between about 250° C. and about 600° C., and preferably between about 300° C. and 450° C. The reaction generally takes place at atmospheric pressure, but the usable pressures may be those which fall within the approximate range of $10^4$ $N/m^2$ to $10^7$ $N/m^2$. The molar ratio of xylene to ethylene will be most preferably within the approximate range of 1:1 to 10:1. The reaction may be suitably accomplished utilizing a feed weight hourly space velocity (WHSV) of between about 0.1 and 100, preferably between about 1 and 20.

The process of this invention may be conducted with the organic reactants in either the gaseous or the liquid phase, or both. It may be carried out as a batch type, semi-continuous or continuous operation utilizing a fixed, fluidized, or moving bed catalyst system.

The following examples are presented for the purpose of illustrating the process of our invention. They should not, however, be construed as imposing undue limitations thereon.

EXAMPLE 1

Alkylation of isomeric dimethylbenzenes

A catalyst comprising 4.0 g of HZSM-5 (65% on alumina) was placed in a flow reactor and heated to 350° C. A feed stream consisting of mixed dimethylbenzenes (22% ortho, 55% meta, 23% para) and ethylene at a molar ratio of 3.5/1 was passed across the catalyst at a weight hourly space velocity (WHSV) of 8.6/0.65 dimethylbenzene/ethylene and atmospheric pressure. The results are shown in Table II below.

TABLE II

| Catalyst | HZSM-5 | HZSM-5 |
|---|---|---|
| Time on Stream (hrs) | 0.5 | 2.0 |
| Liquid Effluent Analysis, wt %: | | |
| Benzene | 0.14 | 0.10 |
| Toluene | 1.05 | 0.94 |
| Dimethylbenzenes: | | |
| 1,2- | 19.74 | 19.52 |
| 1,3- | 46.40 | 45.56 |
| 1,4- | 18.90 | 18.38 |
| Ethyltoluenes | 1.68 | 1.67 |
| 1,3,5-Trimethylbenzene | 0.05 | 0.04 |
| 1,2,4-Trimethylbenzene | 0.40 | 0.32 |
| Dimethylethylbenzenes: | | |
| 2,3- | 0.19 | 0.21 |

TABLE II-continued

| Catalyst | HZSM-5 | HZSM-5 |
|---|---|---|
| 2,4- | 1.01 | 1.23 |
| 2,5- | 0.71 | 0.84 |
| 3,4- | 6.52 | 8.09 |
| 3,5- | 0.51 | 0.59 |
| Other | 2.70 | 2.51 |
| Total | 100 | 100 |
| Selectivity, %: | | |
| 3,4-DMEB/ϵ DMEB | 72.9 | 73.9 |
| 3,4-DMEB/ϵ Products | 48.0 | 50.0 |

EXAMPLE 2

(Comparison)

All conditions were identical to Example 1 except the catalyst was 4.0 g of an amorphous silica-alumina cracking catalyst having 90/10 $SiO_2/Al_2O_3$. The results are shown in Table III below.

TABLE III

| Catalyst | Amorphous Silica Alumina | Amorphous Silica Alumina |
|---|---|---|
| Time on Stream (hrs) | 0.5 | 1.0 |
| Liquid Effluent Analysis, wt %: | | |
| Benzene | 0.05 | — |
| Toluene | 0.50 | 0.44 |
| Dimethylbenzenes: | | |
| 1,2- | 21.53 | 21.62 |
| 1,3- | 50.83 | 51.27 |
| 1,4- | 20.86 | 20.92 |
| Ethyltoluenes | 0.18 | 0.10 |
| 1,3,5-Trimethylbenzene | 0.19 | 0.17 |
| 1,2,4-Trimethylbenzene | 0.52 | 0.40 |
| Dimethylethylbenzenes: | | |
| 2,3- | 0.16 | 0.17 |
| 2,4- | 0.95 | 0.90 |
| 2,5- | 0.94 | 0.87 |
| 3,4- | 1.38 | 1.24 |
| 3,5- | 1.42 | 1.25 |
| Other | 0.49 | 0.65 |
| Total | 100 | 100 |
| Selectivity, %: | | |
| 3,4-DMEB/ϵ DMEB | 28.5 | 28.0 |
| 3,4-DMEB/ϵ Products | 21.6 | 21.0 |

As will be seen from a comparison of Examples 1 and 2, both the total yield of 3,4-DMEB and the selectivity to 3,4-DMEB relative to other isomers of DMEB have been dramatically affected by the HZSM-5 catalyst. Selectivity to the 3,4-isomer in the ZSM-5 system of Example 1 has been enhanced 260% relative to the amorphous silica-alumina system (Example 2) run under identical conditions.

EXAMPLE 3

(Comparison)

The catalyst of Example 1 was replaced with 4.0 g of H-Mordenite (Zeolon-200H) which had been calcined at 520° C. for 8 hours prior to use. The operating parameters of the reaction were otherwise identical to those of the previous examples. The results are shown in Table IV below.

TABLE IV

| Catalyst | H—Mordenite | H—Mordenite |
|---|---|---|
| Time on Stream (hrs) | 0.33 | 1.0 |
| Liquid Effluent Analysis, wt %: | | |
| Benzene | 0.09 | — |
| Toluene | 1.98 | 0.08 |
| Dimethylbenzenes: | | |
| 1,2- | 19.30 | 23.23 |
| 1,3- | 46.33 | 54.38 |
| 1,4- | 17.43 | 21.57 |
| Ethyltoluenes | 1.06 | — |
| 1,3,5-Trimethylbenzene | 0.29 | — |
| 1,2,4-Trimethylbenzene | 2.64 | — |
| Dimethylethylbenzenes: | | |
| 2,3- | 0.18 | — |
| 2,4- | 1.72 | 0.12 |
| 2,5- | 1.63 | 0.11 |
| 3,4- | 3.44 | 0.26 |
| 3,5- | 1.20 | — |
| Other | 2.71 | 0.25 |
| Total | 100 | 100 |
| Selectivity, %: | | |
| 3,4-DMEB/ϵ DMEB | 42.1 | 53.1 |
| 3,4-DMEB/ϵ Products | 22.1 | 45.6 |

As will be seen from the above results, the H-Mordenite catalyst aged quickly while on-stream and produced an isomeric mixture of dimethylethylbenzenes.

EXAMPLE 4

(Comparison)

Rare earth-exchanged Zeolite-Y (REY) was tested under conditions identical to those of Example 1. The catalyst had been calcined for 20 hours at 520° C. prior to use. The results are summarized in Table V.

TABLE V

| Catalyst | REY | REY |
|---|---|---|
| Time on Stream (hrs) | 0.33 | 1.50 |
| Liquid Effluent Analysis, wt %: | | |
| Benzene | 0.23 | 0.09 |
| Toluene | 7.20 | 3.14 |
| Dimethylbenzenes: | | |
| 1,2- | 11.60 | 17.46 |
| 1,3- | 35.23 | 45.84 |
| 1,4- | 13.66 | 17.47 |
| Ethyltoluenes | 4.56 | 1.28 |
| 1,3,5-Trimethylbenzene | 2.79 | 0.84 |
| 1,2,4-Trimethylbenzene | 9.80 | 4.13 |
| Dimethylbenzenes: | | |
| 2,3- | 0.29 | 0.25 |
| 2,4- | 1.66 | 1.42 |
| 2,5- | 1.57 | 1.28 |
| 3,4- | 2.99 | 2.46 |
| 3,5- | 3.40 | 2.23 |
| Other | 5.02 | 2.11 |
| Total | 100 | 100 |
| Selectivity, %: | | |
| 3,4-DMEB/ϵ DMEB | 30.2 | 32.2 |
| 3,4-DMEB/ϵ Products | 7.7 | 12.7 |

Again, it will be seen that selectivity to the 3,4-DMEB is significantly less than that obtained with the HZSM-5 catalyst of Example 1.

EXAMPLE 5

(Comparison)

Identical in all respects with Example 1 except in this instance the catalyst was 4.0 g of HZSM-12 zeolite. The results are shown in Table VI below.

TABLE VI

| Catalyst | HZSM-12 | HZSM-12 |
|---|---|---|
| Time on Stream (hrs) | 0.50 | 1.0 |

TABLE VI-continued

| Catalyst | HZSM-12 | HZSM-12 |
|---|---|---|
| Liquid Effluent Analysis, wt %: | | |
| Benzene | 0.13 | 0.08 |
| Toluene | 4.40 | 2.11 |
| Dimethylbenzenes: | | |
| 1,2- | 18.02 | 20.48 |
| 1,3- | 42.40 | 48.74 |
| 1,4- | 16.59 | 18.73 |
| Ethyltoluenes | 1.54 | 0.62 |
| 1,3,5-Trimethylbenzene | 1.00 | 0.33 |
| 1,2,4-Trimethylbenzene | 3.75 | 1.75 |
| Dimethylethylbenzenes: | | |
| 2,3- | 0.22 | 0.13 |
| 2,4- | 1.64 | 1.18 |
| 2,5- | 1.62 | 1.18 |
| 3,4- | 2.97 | 2.10 |
| 3,5- | 2.66 | 1.36 |
| Other | 3.06 | 1.21 |
| Total | 100 | 100 |
| Selectivity, %: | | |
| 3,4-DMEB/ϵ DMEB | 32.6 | 35.3 |
| 3,4-DMEB/ϵ Products | 14.9 | 19.4 |

A side-by-side comparison of Table II (Example 1, HZSM-5) with Table VI above (HZSM-12) reveals an unexpected clear and substantial superiority of the ZSM-5 catalyst over the ZSM-12 catalyst with respect to selectivity to 3,4-DMEB as the product of choice in the ethylation of dimethylbenzenes.

EXAMPLES 6-12

Effect of Steaming the Catalyst

The effects of steaming the catalyst for various time periods on the conversion and selectivities for alkylation were studied and the results are summarized in Table VII below. The steamed catalysts were prepared by passing a stream of water vapor over the catalyst at 4.3 cm$^3$/hr and 600° C. The water stream was shut off after steaming for the desired time and the temperature reduced to 550° C. The catalyst was then dried in flowing air at 550° C. for 30 minutes. In each example the catalyst comprised 4.0 g of HZSM-5 (65% on alumina) and the operating parameters were the same as in Example 1—i.e. mixed dimethylbenzenes (22% ortho, 55% meta, 23% para) and ethylene at a 3.5/1 molar ratio; WHSV 8.6/0.65; reaction temperature 350° C.; atmospheric pressure.

TABLE VII

Effect of Steaming

| Example | Hours Steamed | 3,4-DMEB ϵ DMEB | 3,4-DMEB ϵ Products |
|---|---|---|---|
| 6 | None | 71.5% | 46.7% |
| 7 | 0.50 | 91.5 | 69.7 |
| 8 | 1.00 | 91.4 | 75.3 |
| 9 | 1.25 | 93.0 | 79.5 |
| 10 | 1.50 | 92.5 | 80.1 |
| 11 | 1.75 | 92.5 | 81.1 |
| 12 | 2.25 | 92.5 | 81.2 |

Steaming the catalyst prior to use is shown to dramatically increase the selectivity to 3,4-DMES product. A similar effect may be obtained by depositing a coating of coke on the catalyst prior to use, or by a combination of precoking and steaming the catalyst.

EXAMPLES 13-15

Alkylation of Individual Isomers of Dimethylbenzene

These examples demonstrate that the selectivity to 3,4-DMEB is independent of the dimethylbenzene isomer which is used as starting material. All of the run conditions were the same as in Example 1 with the exception that the dimethylbenzene feed was substantially the isomer as indicated in Table VIII below. The catalyst was 4.0 g of HZSM-5 which had been steamed for 1.75 hours at 600° C. prior to use and the DMEB-/Ethylene feed WHSV was 8.6/0.65 at atmospheric pressure and 350° C.

TABLE VIII

Ethylation of Dimethylbenzene Isomers

| Example: | 13 | 14 | 15 |
|---|---|---|---|
| Dimethylbenzene Isomer: | 1,2- | 1,3- | 1,4- |
| Liquid Products: | | | |
| Dimethylbenzenes: | | | |
| 1,2- | 65.46 | 6.00 | 2.79 |
| 1,3- | 15.44 | 69.10 | 17.89 |
| 1,4- | 4.44 | 7.40 | 65.63 |
| 3,4-DMEB | 10.43 | 13.22 | 10.28 |
| Total DMEB | 10.97 | 14.12 | 10.88 |
| Other | 3.69 | 3.38 | 2.8 |
| Selectivity, %: | | | |
| 3,4-DMEB/ϵ DMEB | 95.1 | 93.6 | 94.5 |
| 3,4-DMEB/ϵ Products | 71.1 | 75.5 | 75.1 |

The foregoing data clearly establish that the dimethylbenzene isomers do not come to equilibrium under the conditions of the reaction. What is more, the selectivity to 3,4-DMEB products is shown to be very high regardless of the isomeric structure of the dimethylbenzene starting material.

EXAMPLES 16-18

Effect of Catalyst Crystal Size

The effect of crystal size on the selectivities and conversion are illustrated by the following examples, wherein samples of HZSM-5 catalyst of three different crystal sizes were studied. The runs were carried out at 350° C. and atmospheric pressure, the feed stream comprising ethylene and mixed dimethylbenzenes (22% ortho, 55% meta, 23% para). The reactant feed rates and nominal crystal sizes of the zeolite catalysts are given in Table IX below, as are the test results.

TABLE IX

Crystal Size Effect

| Example: | 16 | 17 | 18 |
|---|---|---|---|
| Catalyst: | HZSM-5 | HZSM-5 | HZSM-5 |
| Nominal Crystal Size (microns): | 0.02-0.05 | 0.2-0.5 | 1-2 |
| WHSV: | | | |
| Dimethylbenzene | 4.4 | 8.6 | 5.7 |
| Ethylene | 0.60 | 0.65 | 0.83 |
| Time on Stream (hrs): | 6 | 2 | 1 |
| Ethylene Conversion, mole %: | 46.8 | 39 | 6.9 |
| Selectivity, %: | | | |
| 3,4-DMEB/ϵ DMEB | 75.1 | 73.8 | 88.1 |
| 3,4-DMEB/ϵ Products | 76.9 | 50.0 | 26.9 |

The foregoing illustrates that the overall selectivity to 3,4-DMEB among all products and the rate of conversion are relatively higher for the smaller crystal size zeolites. That is to say, with respect to HZSM-5, 0.02–0.05μ > 0.02–0.05μ > 1–2μ. However, the selectivity to 3,4-DMEB relative to all DMEB isomers produced is shown to increase with increasing crystal size.

The foregoing examples are intended to be merely illustrative of the invention disclosed herein and to graphically demonstrate the remarkable shape selectivity of the reaction. It is to be understood that there will be many variations thereon which may be made by those skilled in the art without departing from the scope and the spirit of the following claims.

We claim:

1. A process for alkylation and rearrangement, whereby a mixture of three isomers of dimethylbenzene is alkylated with ethylene to produce dimethylethylbenzene, wherein methyl groups on benzene rings of said dimethylethylbenzene are rearranged such that there is produced a product containing 3,4-dimethyl-1-ethylbenzene in excess of its normal equilibrium concentration, said process comprising contacting said dimethylbenzene mixture with said ethylene under conditions effective for accomplishing said alkylation in the presence of a crystalline zeolite ZSM-5 catalyst, said zeolite having a silica to alumina ratio of at least about 12, wherein said dimethylethylbenzene contains at least 71.5% of 3,4-dimethyl-1-ethylbenzene.

2. The process of claim 1 wherein said conditions effective for accomplishing said alkylation reaction comprise a temperature of about 250° C. to about 600° C. and a pressure within the approximate range of $10^4$ $N/m^2$ to $10^7$ $N/m^2$.

3. The process of claim 1 wherein said conditions effective for accomplishing said alkylation reaction comprise a temperature of between about 300° C. and about 450° C. and a pressure within the approximate range of $10^5$ $N/m^2$ to $4 \times 10^6$ $N/m^2$.

4. The process of claim 1 wherein said mixture of dimethylbenzene isomers contains at least 55% of the meta-isomer and at least 23% of the para-isomer.

5. The process of claim 1 wherein said ZSM-5 comprises crystals of less than 1 micron in size.

6. The process of claim 1, wherein said zeolite catalyst is modified prior to use by steaming.

7. The process of claim 1, wherein said zeolite catalyst is modified prior to use by depositing between about 2% and about 75% by weight of coke thereon.

8. The process of claim 1, wherein said zeolite catalyst is combined in an amount between about 1 and about 90 weight percent with a binder therefor.

9. The process of claim 9 wherein said zeolite catalyst is modified prior to use by steaming.

10. The process of claim 9 wherein said zeolite catalyst is modified prior to use by depositing between about 2% and about 75% by weight of coke thereon.

11. The process of claim 1, wherein said mixture of dimethylbenzene isomers contains no more than 22% of the ortho-isomer.

12. A process for converting meta-isomers and para-isomers of dimethylbenzene in a dimethylbenzene gas to 3,4-dimethyl-1-ethylbenzene, said process comprising contacting said dimethylbenzene gas with ethylene under conditions effective for accomplishing alkylation in the presence of a crystalline zeolite ZSM-5 catalyst, said zeolite having a silica to alumina ratio of at least about 12, wherein 3,4-dimethyl-1-ethylbenzene constitutes at least 71.5% of the dimethylethylbenzene produced.

13. The process of claim 12 wherein said conditions effective for accomplishing said alkylation reaction comprise a temperature of about 250° C. to about 600° C. and a pressure within the approximate range of $10^4$ $N/m^2$ to $10^7$ $N/m^2$.

14. The process of claim 12 wherein said conditions effective for accomplishing said alkylation reaction comprise a temperature of between about 300° C. and about 450° C. and a pressure within the approximate range of $10^5$ $N/m^2$ to $4 \times 10^6$ $N/m^2$.

15. The process of claim 12 wherein said ZSM-5 comprises crystals of less than 1 micron in size.

16. The process of claim 12 wherein said zeolite catalyst is modified prior to use by steaming.

17. The process of claim 12 wherein said zeolite catalyst is modified prior to use by depositing between about 2% and about 75% by weight of coke thereon.

18. The process of claim 12 wherein said zeolite catalyst is combined in an amount between about 1 and about 90 weight percent with a binder therefor.

19. The process of claim 18 wherein said zeolite catalyst is modified prior to use by steaming.

20. The process of claim 18 wherein said zeolite catalyst is modified prior to use by depositing between about 2% and about 75% by weight of coke thereon.

21. The process of claim 12, wherein said dimethylbenzene gas contains no more than 22% of the ortho-isomer.

22. The process of claim 12, wherein said dimethylbenzene gas contains 22% of the ortho-isomer, 55% of the meta-isomer, and 23% of the para-isomer.

23. A process for the selective alkylation of dimethylbenzene with ethylene to produce 3,4-dimethyl-1-ethylbenzene in excess of its normal equilibrium concentration, said process comprising contacting said dimethylbenzene with said ethylene under conditions effective for accomplishing said alkylation in the presence of a crystalline zeolite ZSM-5 catalyst, wherein said conditions effective for accomplishing said alkylation reaction comprise a temperature of between about 300° C. and about 450° C. and a pressure within the approximate range of $10^5$ $N/m^2$ to $4 \times 10^6$ $N/m^2$, whereby the percent selectivity in terms of the amount of 3,4-dimethyl-1-ethylbenzene produced as compared with the total dimethyl-ethylbenzene produced is at least 260% greater than the corresponding percent selectivity measured in a reaction wherein said ZSM-5 catalyst of said process is replaced with an amorphous silica-alumina cracking catalyst having 90/10 $SiO_2/Al_2O_3$ and the process with the silica alumina catalyst is run under identical conditions as the process with the ZSM-5 catalyst.

* * * * *